(12) United States Patent
Litzie et al.

(10) Patent No.: US 7,022,099 B2
(45) Date of Patent: Apr. 4, 2006

(54) EXTRACORPOREAL BLOOD HANDLING SYSTEM WITH AUTOMATIC FLOW CONTROL AND METHODS OF USE

(75) Inventors: A. Kenneth Litzie, Tustin Ranch, CA (US); Steven K. Stringer, Los Gatos, CA (US); Mehrdad Farhangnia, Sunnyvale, CA (US); Muslim Tyebjee, Sunnyvale, CA (US); Thomas A. Afzal, Menlo Park, CA (US); Ben F. Brian, III, Menlo Park, CA (US)

(73) Assignee: Cardiovention, Inc., Santa Clara, CA (US)

( * ) Notice: Subject to any disclaimer, the term of this patent is extended or adjusted under 35 U.S.C. 154(b) by 88 days.

(21) Appl. No.: 10/392,441

(22) Filed: Mar. 17, 2003

(65) Prior Publication Data

US 2004/0184953 A1 Sep. 23, 2004

(51) Int. Cl.
*A61M 37/00* (2006.01)
*A61M 1/14* (2006.01)
*A61M 1/34* (2006.01)
*B01D 35/16* (2006.01)
*B01D 24/00* (2006.01)

(52) U.S. Cl. ............... 604/6.09; 604/4.01; 604/6.1; 422/44; 128/DIG. 3; 210/348; 210/416.1

(58) Field of Classification Search ............ 210/85–88, 210/90, 97, 98, 103, 104, 188, 739, 741, 210/348, 416.1, 321.6; 604/4.01, 5.01, 6.01, 604/6.1, 6.09, 6.11, 6.16, 7, 65, 67, 73, 122, 604/405, 406; 422/44–48; 128/DIG. 3; 261/19, 261/24, 26, 28–30, 87, 83–85, 106, 109, 261/110
See application file for complete search history.

(56) References Cited

U.S. PATENT DOCUMENTS

| | | | |
|---|---|---|---|
| 3,701,433 A | 10/1972 | Krakauer et al. | |
| 3,827,562 A | 8/1974 | Esmond | |
| 4,056,476 A | 11/1977 | Mouwen et al. | |

(Continued)

FOREIGN PATENT DOCUMENTS

DE 4326886 2/1995

OTHER PUBLICATIONS

3M Health Care, "Sarns Delphin II Centrifugal System", Operators Manual, Nov. 1993, pp. 1–26, Ann Arbor US.
3M Health Care, "3M Sarns Modular Perfusion System 8000", Operators Manual, circa 1993, pp. 1.1–9.9.
Stockert Instrumente GmbH, "S3 System Heart Lung Machine Modular System", Operator's Manual, 1994, pp. I–XVII and 2.1–5.86, Munich Germany.
3M Health Care, "Sarns Ultrasonic Air Sensors", Operators Manual, Nov. 1994, pp. 1–22, Ann Arbor US.
David W. Fried et al., "Single Pump Mechanically Aspirated Venous Drainage (SPMAVD) for Cardiac Reoperation", Perfusion, 1995, pp. 327–332, vol. 10, Edward Arnold, UK.

(Continued)

*Primary Examiner*—Patricia Bianco
(74) *Attorney, Agent, or Firm*—Nicola A. Pisano, Esq.; Luce, Forward, Hamilton & Scripps LLP

(57) ABSTRACT

Apparatus for processing blood in an extracorporeal circuit with automatic flow control is provided in which error conditions are sensed and system operation is modulated responsive to the error conditions. The apparatus includes an extracorporeal blood processing system, at least one sensor that senses the presence or absence of gas or monitors venous pressure, and a controller operably coupled to the blood processing system to selectively reduce pump speed or to reconfigure flow paths within the blood processing system responsive to the sensor output.

26 Claims, 14 Drawing Sheets

U.S. PATENT DOCUMENTS

| | | | |
|---|---|---|---|
| 4,087,363 A | | 5/1978 | Rosemeyer et al. |
| 4,111,829 A | | 9/1978 | Bimond et al. |
| 4,126,558 A | | 11/1978 | Luceyk |
| 4,157,965 A | | 6/1979 | Raible |
| 4,164,468 A | | 8/1979 | Raible |
| 4,280,495 A | | 7/1981 | Lampert |
| 4,283,289 A | | 8/1981 | Meyst et al. |
| 4,319,580 A | | 3/1982 | Colley et al. |
| 4,354,500 A | | 10/1982 | Colley et al. |
| 4,354,501 A | | 10/1982 | Colley et al. |
| 4,354,502 A | | 10/1982 | Colley et al. |
| 4,401,566 A | | 8/1983 | Igari et al. |
| 4,411,783 A | | 10/1983 | Dickens et al. |
| 4,490,254 A | | 12/1984 | Gordon et al. |
| 4,490,331 A | | 12/1984 | Steg, Jr. |
| 4,493,705 A | | 1/1985 | Gordon et al. |
| 4,572,724 A | | 2/1986 | Rosenberg et al. |
| 4,653,577 A | | 3/1987 | Noda |
| 4,662,906 A | | 5/1987 | Matkovich et al. |
| 4,676,771 A | | 6/1987 | Henke |
| 4,690,762 A | | 9/1987 | Katsura |
| 4,698,207 A | | 10/1987 | Bringham et al. |
| 4,747,826 A | | 5/1988 | Sassano |
| 4,876,066 A | | 10/1989 | Bringham et al. |
| 4,919,802 A | | 4/1990 | Katsura |
| 4,923,438 A | | 5/1990 | Vasconcellos et al. |
| 4,981,413 A | | 1/1991 | Elonen et al. |
| 5,011,469 A | | 4/1991 | Buckberg et al. |
| 5,017,103 A | | 5/1991 | Dahl |
| 5,055,198 A | | 10/1991 | Shettigar |
| 5,158,533 A | | 10/1992 | Strauss et al. |
| 5,162,102 A | | 11/1992 | Nogawa et al. |
| 5,188,604 A | * | 2/1993 | Orth ........................ 604/153 |
| 5,205,153 A | | 4/1993 | Hlavinka et al. |
| 5,232,437 A | | 8/1993 | Lysaght et al. |
| 5,266,265 A | | 11/1993 | Raible |
| 5,270,005 A | * | 12/1993 | Raible ........................ 422/46 |
| 5,334,309 A | | 8/1994 | Huggett et al. |
| 5,394,732 A | | 3/1995 | Johnson et al. |
| 5,411,472 A | | 5/1995 | Steg, Jr. et al. |
| 5,445,613 A | | 8/1995 | Orth |
| 5,503,801 A | | 4/1996 | Brugger |
| 5,514,335 A | | 5/1996 | Leonard et al. |
| 5,591,251 A | | 1/1997 | Brugger |
| 5,632,894 A | | 5/1997 | White et al. |
| 5,634,892 A | | 6/1997 | Whalen |
| 5,651,765 A | | 7/1997 | Haworth et al. |
| 5,746,575 A | | 5/1998 | Westphal et al. |
| 5,762,684 A | | 6/1998 | Hayahi et al. |
| 5,823,986 A | | 10/1998 | Peterson |
| 5,840,068 A | | 11/1998 | Cartledge |
| 5,863,179 A | | 1/1999 | Westphal et al. |
| 5,876,611 A | | 3/1999 | Shettigar |
| 5,899,873 A | | 5/1999 | Jones et al. |
| 5,997,816 A | | 12/1999 | McIntosh et al. |
| 6,017,493 A | | 1/2000 | Cambron et al. |
| 6,206,632 B1 | | 3/2001 | Gallus |
| 6,224,829 B1 | * | 5/2001 | Piplani et al. ................ 422/45 |
| 6,241,945 B1 | | 6/2001 | Owen |
| 6,267,926 B1 | | 7/2001 | Reed et al. |
| 6,302,860 B1 | * | 10/2001 | Gremel et al. ............. 604/6.09 |
| 6,315,751 B1 | | 11/2001 | Cosgrove et al. |
| 6,328,712 B1 | | 12/2001 | Cartledge |
| 6,337,049 B1 | | 1/2002 | Tamari |
| 6,508,859 B1 | | 1/2003 | Zia et al. |
| 6,524,267 B1 | | 2/2003 | Gremel et al. |
| 6,730,267 B1 | | 5/2004 | Stringer et al. |

OTHER PUBLICATIONS

John M. Toomasian et al., "Total Extrathoracic Cardiopulmonary Support with Kinetic Assisted Venous Drainage: Experience in 50 Patients", Perfusion, 1998, pp. 137–143, vol. 13, Edward Arnold, UK.

Jostra, "Heart Lung Machine HL 20", User Manual, circa 1998, pp. i–vi and 1.1–6.6, Germany.

Matayoshi et al., "Development of a Completely Close Circuit Using an Air Filter in a Drainage Circuit for Minimally Invasive Cardiac Surgery," Artificial Organs 24(6): 454–458 (2000).

Medtronic, "The Bio–Pump.TRM. Centrifugal Blood Pump." (1998).

Morita et al., "Closed Circuit Cardiopulmonary Bypass with Centrifugal Pump for Open–Heart Surgery: New Trial for Air Removal," Artifical Organs 24(6):442–445 (2000).

Jorge Ojita, et al., "Assisted Venous Drainage Cardiopulmonary Bypass in Congenital Heart Surgery," Ann. Thorac. Surg., 71:1267–72 (2001).

Joseph J. Sistino et al., "Laboratory Evaluation of a Low Prime Closed Circuit Cardiopulmonary Bypass Sstem," J. Extra–Corp. Tech., 24(4):116–119 (1993).

Declaration of Jorge Ojito, Aug. 2003.

Declaration of Yehuda Tamari, Sep. 4, 2003.

\* cited by examiner

EXTRACORPOREAL BLOOD HANDLING SYSTEM WITH AUTOMATIC FLOW CONTROL AND METHODS OF USE

FIELD OF THE INVENTION

The present invention relates to an extracorporeal blood handling system with automatic flow control and methods for use for monitoring and detecting error conditions, and modulating flow through the extracorporeal blood handling system in response to the detected error conditions.

BACKGROUND OF THE INVENTION

For more than thirty years, vascular diseases have been treated using open surgical procedures. In 1999 alone, 753,000 open-heart procedures, including coronary artery bypass grafting (CABG), valve replacements, and heart transplants, were performed. During a typical CABG procedure, a sternotomy is performed to gain access to the pericardial sac, the patient is put on cardiopulmonary bypass (CPB), and the heart is stopped using a cardioplegia solution.

Generally, previously-known CPB is accomplished by constructing an extracorporeal blood handling system including, inter alia, a venous line, a venous reservoir, a centrifugal or roller pump that perfuses blood through the extracorporeal circuit and the patient, an oxygenator for oxygenating the blood, an arterial line for returning oxygenated blood to the patient, and an arterial filter located in the arterial line. The pump in previously known methods of CPB is placed after the venous reservoir and the venous flow into the reservoir is driven by negative pressure in this line from a siphon and not the pump. In order to minimize the diameter and cannula size required for the venous line, vacuum is often applied to the reservoir, as described, for example, in U.S. Pat. No. 6,017,493 to Cambron. The use of a venous reservoir provides compliance in the blood treatment system so the venous flow may be controlled independently of the arterial or return flow to the patient.

Previously-known methods of CPB are susceptible to several error or trigger conditions. For instance, one trigger condition is the inadvertent introduction of air into the extracorporeal circuit. This may occur in a number of ways, including inadvertent opening of a vent line, improper priming of the circuit, or by turning the heart during surgery. In addition, differences between blood inflow to a venous reservoir and outflow from the venous reservoir due to the pump head can lead to depletion of the reservoir and the entrainment of large amounts of air. If returned to the patient, air can cause significant patient injury such as brain damage, cardiac dysfunction, and myocardial damage. Further, an air-blood mixture may cause turbulence and high shear stresses within the circuit, resulting in hemolysis and humoral and/or cellular activation.

Previously known CPB systems, such as the S3 System sold by Stockert GmbH, Munich, Germany, the HL 20 Heart Lung Machine sold by Jostra Corp., The Woodlands, Tex., USA and the Sarns Modular Perfusion System 8000, sold by Terumo Cardiovascular Systems, Ann Arbor, Mich., USA, each include a level detector in the venous reservoir that slows and then stops delivery of blood to a patient if the volume of blood in the venous reservoir falls below a minimum volume. Each of these systems also includes a bubble detector that abruptly stops the pump if a predetermined number of bubbles larger than a predetermined size are detected.

The system shutdown strategy used in previously known CPB systems is designed to prevent de-priming of the venous reservoir and other components of the CPB circuit until the perfusionist can correct the problem. Due to the extended periods of time required to prime previously-known CPB systems, such a strategy is critical to avoid de-priming. Unfortunately, this strategy leads to no forward flow to the patient, with potentially serious consequences if flow is not restored promptly.

Another previously-known method for handling air entrained in the blood is described in U.S. Pat. No. 5,188,604 to Orth. The system described in that patent includes an air sensor disposed in the arterial line, a controller, and a series of solenoid-controlled valves, and a shunt circuit. If air is detected in blood passing to the arterial line, the controller actuates the solenoid-controlled valves to stop flow in the arterial line and simultaneously opens the shunt circuit to redirect the air-laden blood back into the blood treatment system. Like the previously-described CPB systems described above, the system described in the Orth patent results in no forward flow to the patient until the error condition is corrected.

Another trigger condition is low venous pressure, which may be caused by occlusions within the circuit. Low venous pressure is a known risk factor for air entrainment and may result in depletion of the venous reservoir as previously discussed, thus requiring blood delivery to the patient to be suspended while the condition is corrected or the CPB system is re-primed.

In addition, substantial occlusion of the venous line in previously-known CPB systems may provide minimal to no reaction time for the perfusionist to correct trigger conditions. For instance, should the venous return flow stop due to a trigger condition, such as detection of a large bubble, the perfusionist has only a few seconds to stop the heart-lung machine before the bubble is pumped into the patient.

Yet another problem with previously-known extracorporeal blood handling systems is the substantial suction force required for proper air evacuation due to an open air source. An open air source enables the pump to pull in large amounts of air, overwhelming the ability of an air evacuation line, if present, to remove the air.

In view of the aforementioned limitations, it would be desirable to provide an extracorporeal blood handling system that monitors and automatically modulates blood flow in response to trigger conditions thereby increasing the time available to the perfusionist to correct trigger conditions.

It also would be desirable to provide an extracorporeal blood handling system that monitors and automatically modulates system operation in response to the detection of gas in the system, to enhance the ability of an air evacuation line to remove the air and avoid de-priming the pump.

It further would be desirable to provide an extracorporeal blood handling system that automatically modulates pump speed in response to the detection of a massive air bolus in the extracorporeal blood circuit.

It still further would be desirable to provide an extracorporeal blood handling system that automatically modulates system operation in response to the detection of discrete trigger conditions, monitors such conditions, and resumes normal operation when the triggering conditions resolve.

It even further would be desirable to provide an extracorporeal blood handling system that automatically modulates pump speed in response to the detection of low venous pressures in the extracorporeal blood circuit.

SUMMARY OF THE INVENTION

In view of the foregoing, it is an object of the present invention to provide an extracorporeal blood handling system that monitors and automatically modulates system operation in response to trigger conditions, thereby increasing the time available for an operator, e.g., the perfusionist, to correct trigger conditions.

It is another object of the present invention to provide an extracorporeal blood handling system that monitors and automatically modulates pump speed in response to the detection of gas in the system, to enhance the ability of an air evacuation line to remove the air and avoid depriming of the pump.

It is an additional object of the present invention to provide an extracorporeal blood handling system that automatically modulates system operation in response to the detection of a massive bolus of air in the circuit.

It is a further object of the present invention to provide an extracorporeal blood handling system that automatically modulates system operation in response to the detection of discrete triggering conditions, such a small amounts of air, monitors such conditions, and resumes normal operation once the triggering conditions subside and/or are acknowledged by the perfusionist.

It is an even further object of the present invention to provide an extracorporeal blood handling system that automatically modulates pump speed in response to the detection of low venous pressures.

These and other objects of the present invention are accomplished by providing an extracorporeal blood handling system with automatic flow control, such as a microprocessor controlled system whereby pump speed is regulated in response to detected trigger conditions.

In a preferred embodiment, the automatic flow control feature of the apparatus is a microprocessor-controlled system that monitors the extracorporeal circuit and automatically modulates pump speed or the system configuration in response to detected trigger conditions. The apparatus comprises an extracorporeal circuit, a controller coupled to an air evacuation system and sensors positioned to sense air and venous pressures within the extracorporeal circuit. The controller is electrically coupled to a pump, such as a centrifugal pump, to modulate the pump speed in response to detected trigger conditions in the extracorporeal circuit.

In a first mode, the automatic flow control system of the present invention comprises a controller coupled to at least one sensor disposed to sense air. Upon sensing a bolus of air, the microprocessor reduces the pump speed to a predetermined lower limit. The predetermined lower limit preferably is determined such that forward blood flow is maintained through the extracorporeal circuit to the patient.

In a second mode, the speed of the centrifugal pump is reduced in response to the detection of discrete amounts of air. In this case, the pump speed is reduced by a predetermined percentage until either the trigger condition is resolved or the pump speed reaches a predetermined lower limit.

In a third mode, the controller is coupled to a second sensor disposed to sense bubbles in the venous line. The speed of the centrifugal pump is reduced in response to the detection of bubbles greater than a predetermined concentration. In this case, the pump speed is reduced by a predetermined percentage until either the trigger condition is resolved or the pump speed reaches a predetermined lower limit.

In a fourth mode, the controller is coupled to a third sensor disposed to sense venous pressure. The speed of the centrifugal pump is reduced in response to the sensing of venous pressure below a predetermined level. In this case, the pump speed is reduced by a fixed step until the venous pressure is no longer below the predetermined level or until a predetermined lower limit is attained.

In alternative embodiments, the system configuration may be altered in response to the detection of trigger conditions, by constricting outflow from the system or by rerouting flowpaths within the system. In accordance with the principles of the present invention, some degree of forward flow to the patient is maintained in these alternative embodiments.

Methods of operating the automatic flow control features of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Overview of a Preferred Blood Handling System

Figure 1:
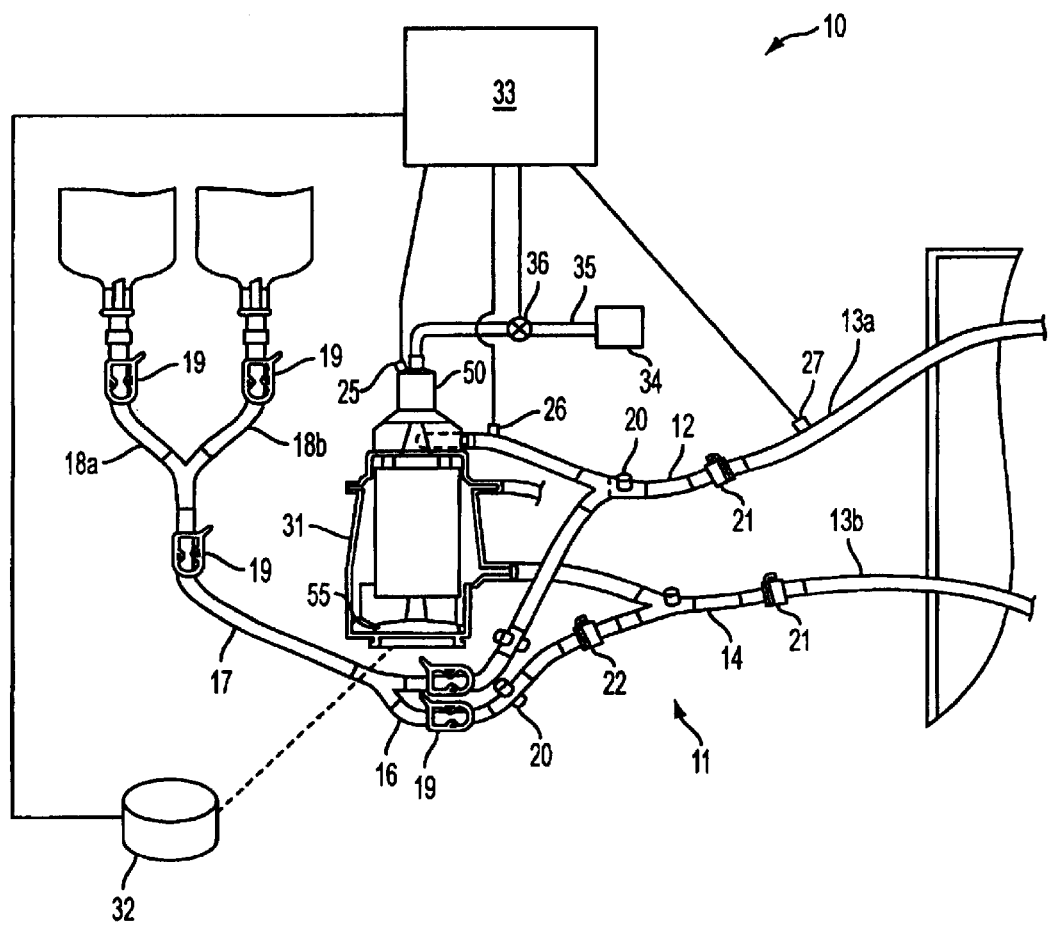
FIG. 1 is a schematic view of a preferred extracorporeal circuit incorporating the automatic flow control system of the present invention.

Referring to FIG. 1, a preferred extracorporeal blood handling system 10 suitable for use with the automatic flow control system of the present invention is described. Extracorporeal blood handling system 10 is designed to maintain a patient on full or partial bypass support, for example, during a coronary artery bypass graft procedure, in either a full-bypass or beating heart (partial bypass) mode of operation, or open heart repair procedure, typically with full-bypass mode of operation.

Extracorporeal blood handling system 10 includes an extracorporeal blood circuit 11 having a perfusion circuit comprising venous line 12, perfusion line segments 13a, 13b and arterial line 14, and a priming/reservoir circuit comprising line 16, priming line 17, and segments 18a and 18b. The ends of perfusion line segments 13a (venous), 13b (arterial) are shown extending into the sterile field as they would appear during use, where they are coupled to venous and arterial cannulae placed in the patient, respectively.

Extracorporeal blood circuit 11 illustratively includes pinch clamps 19 and sampling access ports 20 disposed on various of the lines. Quick-disconnect couplings 21 are provided at the junctions of venous line 12 and venous segment of perfusion line 13a and arterial line 14 and arterial segment of perfusion line 13b. These couplings 21 permit venous line 12 to be directly coupled to arterial line 14 during priming. In addition, another quick-disconnect coupling 22 is provided in line 16 to permit, for example, the inclusion of a heat exchanger when the priming circuit is used for recirculation.

Extracorporeal blood handling system 10 further includes an integrated blood processing component 31 coupled to a drive unit 32 and controller 33. In addition, the blood handling system 10 includes a gas removal system including sensors 25–27, and valve 36 coupled to suction source 34 via line 35. The sensors 25–27, valve 36 and drive unit 32 preferably are electrically coupled to controller 33 so that controller 33 regulates operation of valve 36 and drive unit 32 in response to output of the sensors 25–27. As explained in greater detail hereinafter, the gas removal system of the present invention removes air and other gases from extracorporeal blood circuit 11 and blood processing component 31 during priming and operation of the bypass system.

Figure 2A:
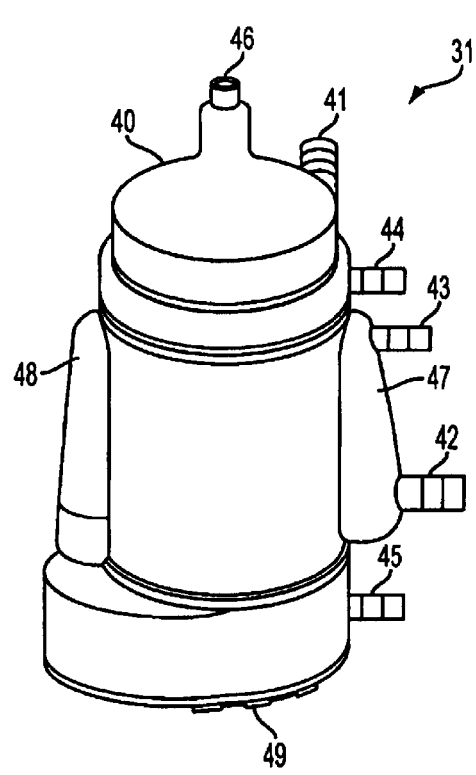
FIGS. 2A and 2B are, respectively, perspective and exploded views of a preferred blood processing component suitable for implementing the automatic flow control features of the present invention.
Figure 2B:
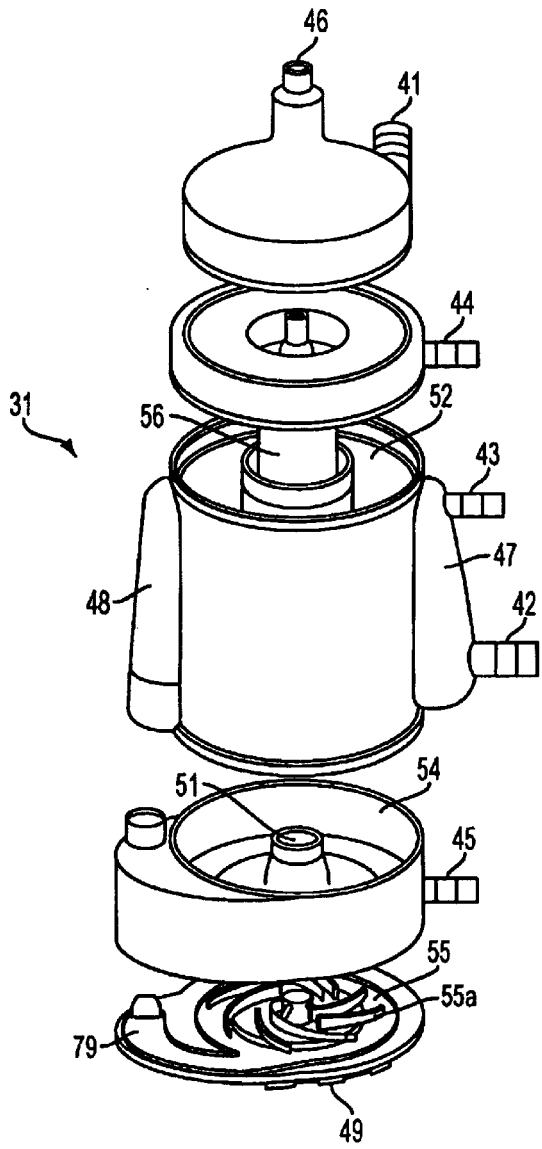
Figure 3:
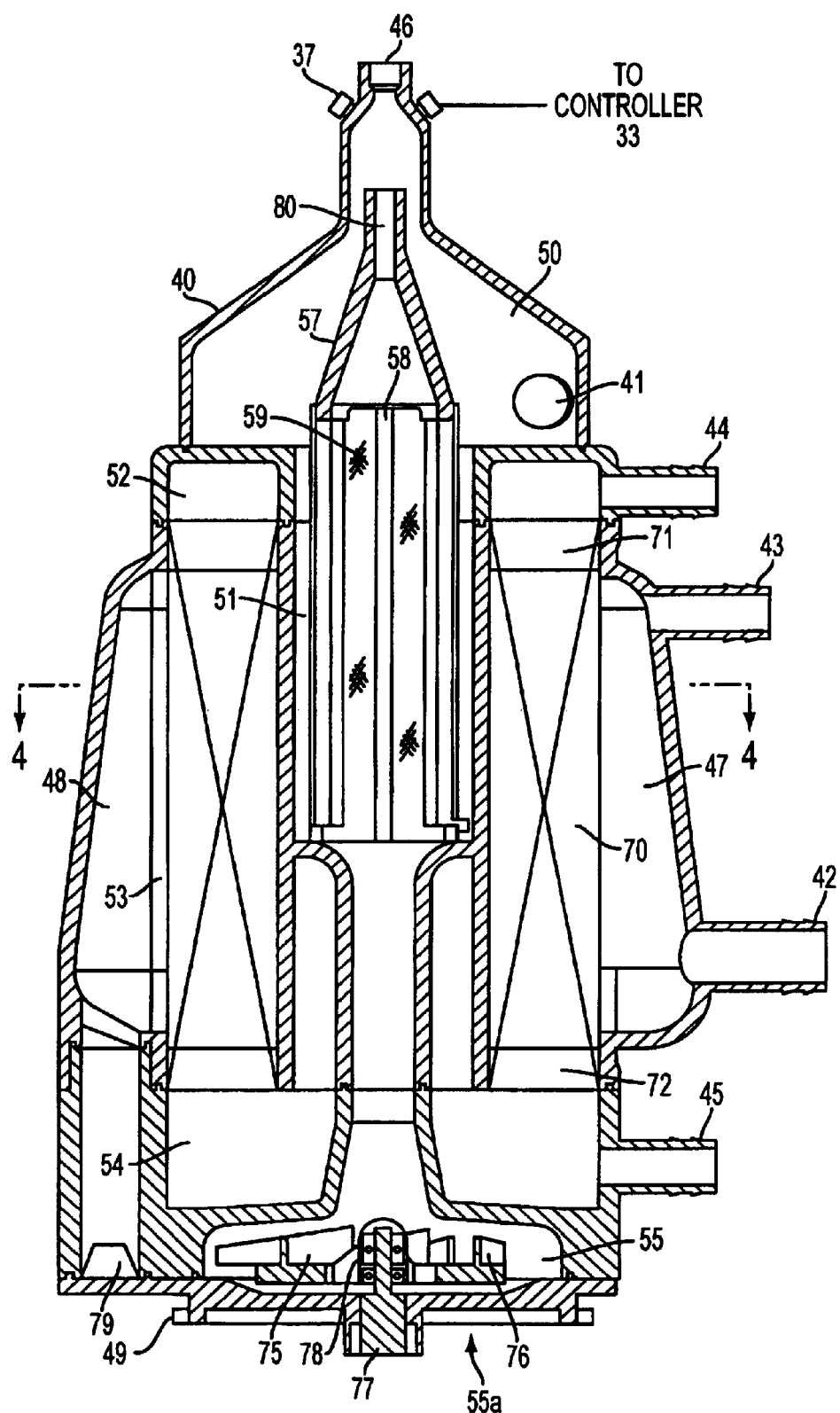
FIG. 3 is a side-sectional view of the blood processing component of FIGS. 2 and 3.

Referring now to FIGS. 2A, 2B and 3, integrated blood processing component 31 provides in a single disposable unit a blood oxygenator, blood pump, and blood filter, and optionally, a heat exchanger and/or arterial filter. Blood processing component 31 includes housing 40 having blood inlet 41, blood outlet 42, recirculation/cardioplegia outlet 43, gas inlet port 44, gas outlet port 45 and gas removal port 46. Blood outlet 42 and recirculation outlet 43 are disposed from blood outlet manifold 47, which is located diametrically opposite blood inlet manifold 48 on housing 40. Blood processing component 31 preferably includes tabs 49 or other means for coupling blood processing component 31 to reusable drive unit 32.

Referring to FIG. 3, housing 40 comprises a series of compartments, including: gas collection plenum 50, central void 51, upper gas plenum 52, annular fiber bundle compartment 53, lower gas plenum 54 and pump space 55. In a preferred embodiment, central void 51 includes a larger diameter upper portion and a smaller diameter lower portion that couples to pump space 55.

Gas collection plenum 50 encloses filter 56 that disposed within upper portion of central void 51. Filter 56 comprises generally conical, fluid impermeable upper wall 57 having outlet 80, baffled support structure 58 and filter material 59. Filter 56 causes gas entrained in blood introduced into the gas collection plenum to separate and collect in the upper portions of gas collection plenum 50. Blood inlet 41 is displaced tangentially relative to the centerline of housing 40, so that blood passing through blood inlet 41 into gas collection plenum 50 swirls around upper wall 57.

Upper wall 57 also preferably has a portion defining an interior chamber that communicates with the upper portion of gas collection plenum 50 through outlet 80. This configuration allows any gas that passes through filter material 59 to escape through outlet 80 in upper wall 57 and be evacuated from gas collection plenum 50. Advantageously, this feature facilitates rapid and easy priming of the blood processing component 31.

Filter material 59 comprises one or multiple layers of a screen-like material, and is mounted to baffled support structure 58. Filter material 59 serves to exclude bubbles from the blood flow by maintaining the swirling action of the blood in the central void for a sufficient time to allow the bubbles to rise to the gas collection plenum. Because the blood circulates around the outside of gas removal/blood filter 56 in central void 51, bubbles impinge against filter material 59 tangentially, and thus "bounce off." Filter material 59 preferably also forms a first stage of a progressive blood filter that is distributed throughout the blood processing component, and filters out relatively large particulate matter.

Figure 4A:
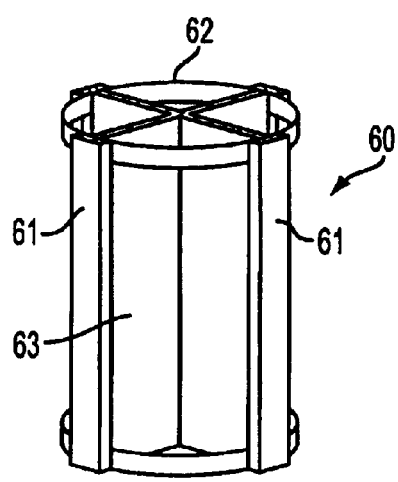
FIGS. 4A and 4B are, respectively, perspective and cross-sectional views of a filter element of the blood processing component of FIG. 3.
Figure 4B:
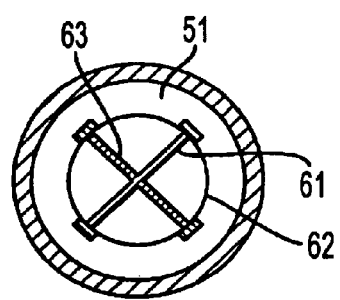

As illustrated in FIGS. 4A and 4B, support structure 58 forms a fluid impermeable cruciform structure 63 having longitudinal struts 61 and support rings 62. Struts 61 serve as baffles to reduce swirling of blood once the blood has passed through filter material 59.

Referring again to FIG. 3, blood oxygenation element 70 is disposed within annular fiber bundle compartment 53, and comprises a multiplicity of gas permeable fibers arranged in an annular bundle. As is well known in the art, the gas permeable fibers are potted near the upper and lower ends of the bundle so gas may pass through the interior of the fibers, while allowing blood to pass along the exterior of the fibers. The bundle of fibers has an upper potting region 71 that separates the blood flow region within the annular bundle from upper gas plenum 52, and lower potting region 72 that separates blood flow region from the lower gas plenum 54.

Blood passing into annular fiber bundle compartment 53 from blood inlet manifold 48 therefore flows through blood oxygenation element 70 and to blood outlet manifold 47. The annular fiber bundle also provides some filtration and de-airing of blood passing through blood processing component 31, by filtering out particulate matter that has passed through filter material 59 employed in gas removal/blood filter 56. Air removal may be facilitated by the microporous structure of the fibers.

The lower portion of central void 51 communicates with pump space 55, in which pump 55a is disposed. In a preferred embodiment, pump 55a is a centrifugal pump including an impeller 75 having a plurality of vanes 76 and is mounted on shaft 77 via bearings 78. Impeller 75 preferably comprises an injection-molded part that encloses a ferromagnetic disk, so that the disk may be magnetically coupled to drive unit 32 (see FIG. 1). Blood accelerated by impeller 75 is ejected from pump space 55 via a passageway that includes curved ramp 79. Ramp 79 serves to redirect radially outward blood flow from impeller to a longitudinal flow within blood inlet manifold 48.

In a preferred embodiment, oxygen is introduced into upper gas plenum 52 through gas inlet port 44 and passes through the interiors of the multiplicity of hollow fibers in blood oxygenation element 70. Carbon dioxide, any residual oxygen, and any other gases exchanged through blood oxygenation element 70 exits into lower gas plenum 54 and are exhausted through gas outlet port 45.

Referring again to FIG. 1, and in accordance with the present invention, the extracorporeal blood handling system 10 also includes sensors 25, 26 and 27 that monitor system parameters. Sensor 25 monitors the level of gas or blood in gas collection plenum 50. Sensor 26 detects the presence of gas in venous line 12, while sensor 27 monitors the pressure in the venous line.

Sensor 25 is configured to sense a parameter indicative of a level or volume of air or other gas, or detect the absence of blood, and preferably operates by a non-contact method. Suitable sensor methods include electrical-charge based, optical and acoustic methods. A resistive contact method also could be employed, in which a low electrical current is passed between adjacent electrodes only in the presence of blood.

Sensor 25 preferably is of a known capacitance type that detects a change in electrical capacitance between the bulk of a liquid (in this case, blood or saline) and gas. Alternatively, sensor 25 may be optical in nature, and uses a light source that has a wavelength that is minimally attenuated by blood. In this case, the light source is directed, at an oblique angle, through the blood towards a photodetector, and sensor 25 is positioned to detect the change in the refractive index of the blood (or saline prime) caused by the presence of air or other gases. In another alternative embodiment, sensors 25 may use an ultrasonic energy source and receiver to detect the presence of gas or absence of blood by the change in acoustic transmission characteristics.

The output of sensor 25 is supplied to controller 33 (see FIG. 1), which in turn regulates valve 36. When sensor 25 outputs a signal indicating that gas is present in the extracorporeal blood handling system 10, controller 33 opens valve 36, thereby coupling gas collection plenum 50 to suction source 34. Suction source 34 may be any suitable suction source such as a vacuum bottle, pump or standard operating room suction port. Once the gas is evacuated, and sensor 25 detects blood at an appropriate level, and changes its output so that controller 33 closes valve 36. In this manner, gas is continuously monitored and then automatically removed from the blood by the blood handling system 10.

Sensor 26 monitors for entrained air in the venous blood and comprises a sensor of the type described with respect to sensor 25. Preferably, sensor 26 uses ultrasound to detect the presence of air entrained in venous blood, and is coupled to controller 33 so that an output of the sensor is used to evaluate one or more trigger conditions, as described hereinafter. Sensor 26 also may be used as a back-up to sensor 25 in the event sensor 25 fails. Sensor 27 may be any suitable pressure sensor such as a piezoelectric transducer or an electrostatic capacitance sensor, and is also coupled to controller 33 and provides an output corresponding to the pressure in venous line 13*a*.

In operation, deoxygenated blood from the sterile field is routed through venous line 12 to blood inlet 41 of integrated blood processing component 31. Blood entering gas collection plenum 50 is induced to circulate around the exterior of filter 56 until air or other gases entrapped in the blood separate out of the blood and collect in the upper portion of the gas collection plenum 50. Responsive to the detection of the presence of a predetermined level or volume of gas by sensor 25, controller 33 controls operation of valve 36 to evacuate the gas.

The gas removal system incorporated in the system of FIGS. 1–3 is capable of removing large amounts of air from extracorporeal blood circuit 11 during initial startup, and may be used to displace the saline prime with the patient's blood thereby greatly reducing the amount of saline (or donor blood) returned to the patient from the prime of the system. Advantageously, this feature facilitates rapid and easy set-up of blood handling system 10, as well as reduces the amount of hemodilution from saline delivered to the patient.

As blood circulates around filter 56 in central void 51, it is drawn by the negative pressure head created by impeller 75 through filter material 59 and down through central void 51 into pump space 55. Rotation of impeller 75 caused by drive unit 32, under the control of controller 33, propels blood up curved ramp 79 into blood inlet manifold 48. From blood inlet manifold 48, the blood traverses blood oxygenation element 70 where it exchanges carbon dioxide and other gases for oxygen. Oxygenated blood then passes into blood outlet manifold 47. Oxygenated blood then is directed back to the sterile field through arterial line 14.

Figure 5:
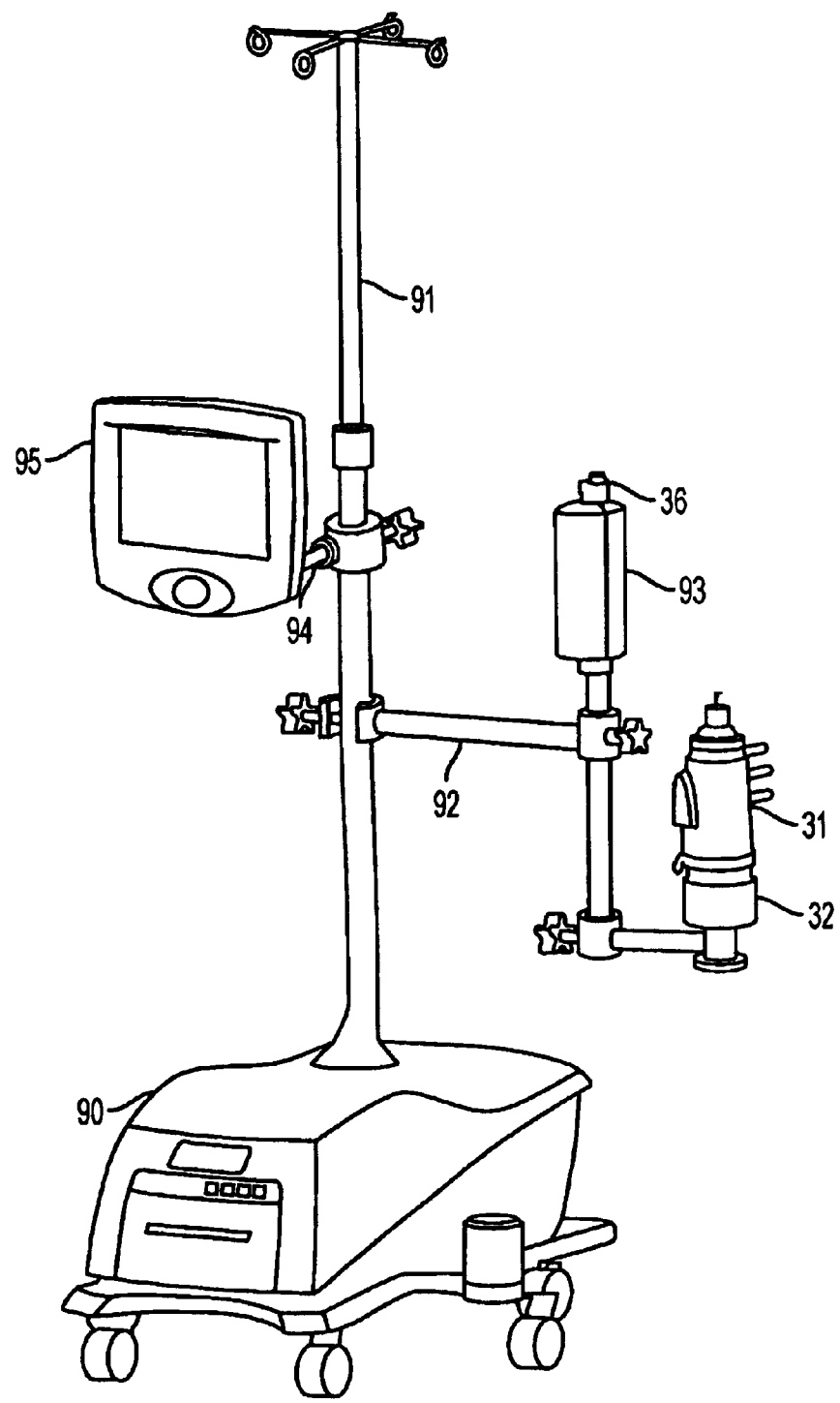
FIG. 5 is a perspective view of a preferred blood handling system incorporating the automatic flow control system of the present invention.

FIG. 5 depicts a preferred embodiment of a blood handling system suitable for implementing the automatic flow control features of the present invention. All blood, gas and electrical lines have been omitted for clarity from FIG. 5, and microprocessor-driven controller 33 (see FIG. 1) and a back-up battery are enclosed in wheeled base 90. Pole 91 is mounted in base 90, and includes support arm 92 that supports blood processing component 31 on drive unit 32. Support arm 92 also carries solenoid 93 that controls valve 36, which is in turn coupled to suction source 34. Pole 91 also carries support arm 93, which carries display screen 95. Screen 95 preferably is a touch-sensitive screen coupled to the controller, and serves as both an input device for the extracorporeal blood handling system 10 and a display of system function.

Figure 6A:
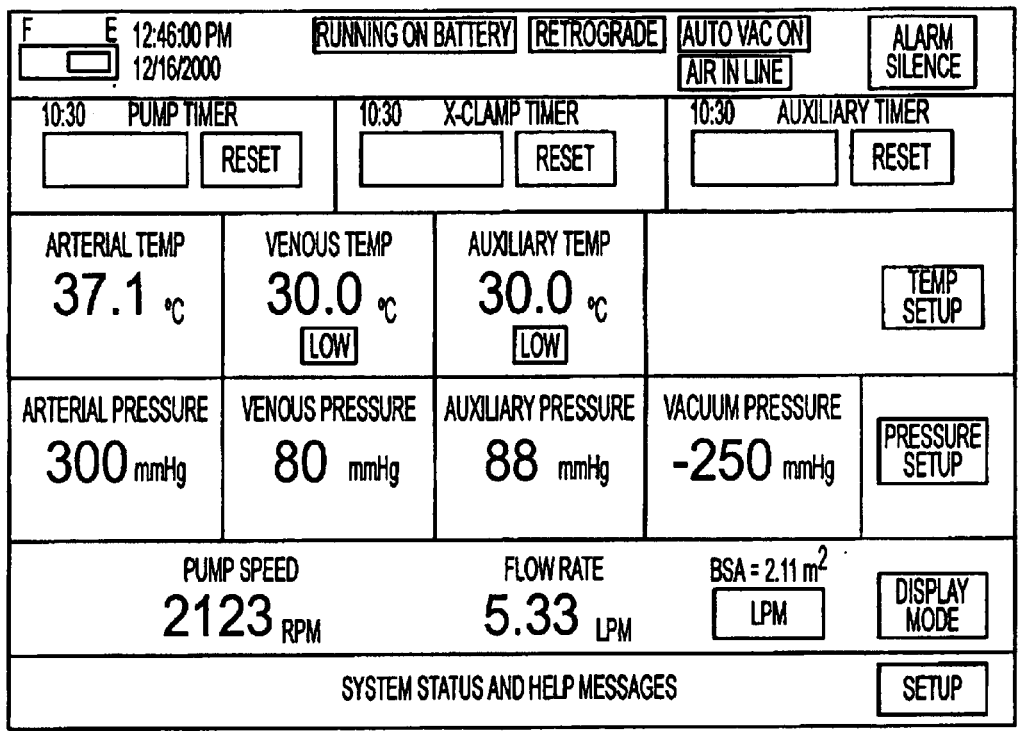
FIGS. 6A and 6B are, respectively, representative screens depicting the display of parameters monitored and/or controlled by the blood processing system of FIG. 5.
Figure 6B:
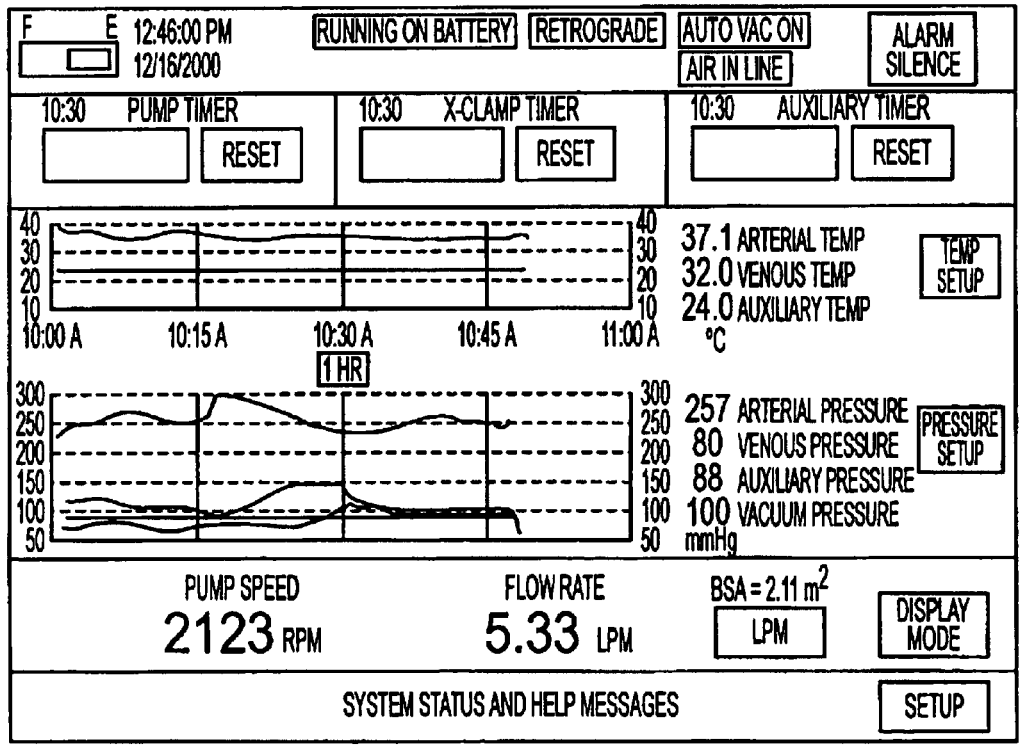

FIGS. 6A and 6B provide representative samples of the information displayed on the main windows of the blood handling system 10. As will of course be understood by one of ordinary skill in the art of computer-controlled equipment, the software used to program operation of the controller may include a number of set-up screens to adjust particular system parameters. FIGS. 6A and 6B are therefore the windows that will most commonly be displayed by the clinician during a procedure.

The display of FIG. 6A includes an indicator of battery status, a series of timers for pump operation, duration of cross-clamping, and an auxiliary timer, arterial and venous temperatures and pressures, the speed of centrifugal pump 55*a* and the corresponding blood flow rate. Preferably, controller 33 is programmed with a number of algorithms for determining an appropriate blood flow rate during the procedure, as determined based on body surface area (BSA). The window also may display the value of BSA determined by the selected algorithm based on the patient's dimensions, and the suggested blood flow rate.

The display of FIG. 6B includes much of the same information provided in the window of FIG. 6A, but further shows temperatures and pressures graphically as well as numerically, so that the clinician can quickly identify trends in the data and take appropriate corrective measures. In addition, a lower portion of the windows displayed in FIGS. 6A and 6B may present system status or help messages, and include touch sensitive buttons that permit access to the other available functions.

Description of the Automatic Flow Control Systems of the Present Invention

In accordance with the principles of the present invention, microprocessor-based controller 33 of the extracorporeal blood handling system 10 of FIG. 1 is programmed to provide at least one automatic flow control feature. More particularly, controller 33 is programmed to evaluate the outputs of sensor 25, 26 and 27 to evaluate the onset or existence of certain trigger conditions and to modulate system operation to avoid adverse impacts to system operation. In a preferred embodiment, modulation of system operation comprises regulating the speed of pump 55a.

For example, the outputs of sensors 25–27 may detect non-negligible levels of gas in the blood and/or low venous pressure, and reduce the speed of pump 55a and the blood flow rate. These reductions are expected to increase the time available for a perfusionist to correct the trigger conditions. In addition, reducing pump speed lengthens the residence time of blood in filter 56, thereby permitting air to be evacuated through valve 36 instead of being drawn through blood processing component 31 by pump 55a.

In a first alternative embodiment, controller 33 may modulate a solenoid-driven clamp on the arterial line to selectively reduce flow rate through the system. The pressure increase in the arterial line created by partially occluding that line is transmitted back to the pump, thereby reducing blood flow through blood processing component 31, and again lengthening the period of time available for the perfusionist to correct the trigger condition or for the trigger condition to resolve.

In yet another embodiment, controller 33 may modulate a solenoid-controlled valve on the priming circuit so that blood is shunted from arterial line 14 back to the inlet of blood processing component 31. Once recirculation is established by opening the valve in the priming circuit, the flow rate through the arterial line will decrease. This decrease in flow will again provide needed time for the perfusionist to correct the trigger condition.

Referring again to FIG. 1, extracorporeal blood handling system 10 with automatic flow control includes extracorporeal blood circuit 11, blood processing component 31, and controller 33. Preferably, the controller 33 includes a microprocessor having software including machine-readable instructions for interpreting sensor input and regulating pump speed and gas removal during automatic flow control.

According to one aspect of the present invention, controller 33 is electrically coupled to drive unit 32 of pump 55a and to sensors 25–27. As disclosed above, the sensors are positioned within extracorporeal blood circuit 11 to detect the presence of air and/or measure venous pressure. Preferably, sensor 25 monitors the level of gas or blood in gas collection plenum 50, sensor 26 detects the presence of gas or blood in venous line 12 and sensor 27 monitors the pressure in venous line 12. When a trigger condition is detected, controller 33 modulates drive unit 32 to lower the speed of pump 55a, thus lowering the blood flow rate through arterial line 14.

Automatic flow control software is programmed to provide a reduction phase, a hold phase and a resume phase in response to a trigger condition. During the reduction phase, pump speed is reduced to lower the rate of blood flow through extracorporeal blood circuit 11. Depending on the type and magnitude of the error condition, pump speed may be reduced by a fixed step, by a percentage of the initial pump speed or by rapidly dropping the pump speed to a predetermined lower limit. In addition, pump speed may be manually regulated.

After reducing the pump speed, the automatic flow control algorithm enters a hold phase, wherein pump speed is maintained at the lower level. In the hold phase, the perfusionist is prompted to enable the resume phase as soon as the trigger condition has been resolved. During the resume phase, pump speed is gradually increased back to the initial level.

The automatic flow control system includes algorithms to implement a number of different control modes of operation. The system preferably will not lower the pump speed below a predetermined lower limit, which is chosen so that forward blood flow is maintained through extracorporeal blood circuit 11 and to the sterile field.

In a preferred embodiment, the automatic flow control system includes a plurality of operational modes that respond to different trigger conditions, including a massive air detection mode, a discrete air detection mode, a bubble detection mode and a low venous pressure detection mode that can operate individually or in combination. These reduction modes are now be described with respect to FIGS. 7–10.

Figure 7:
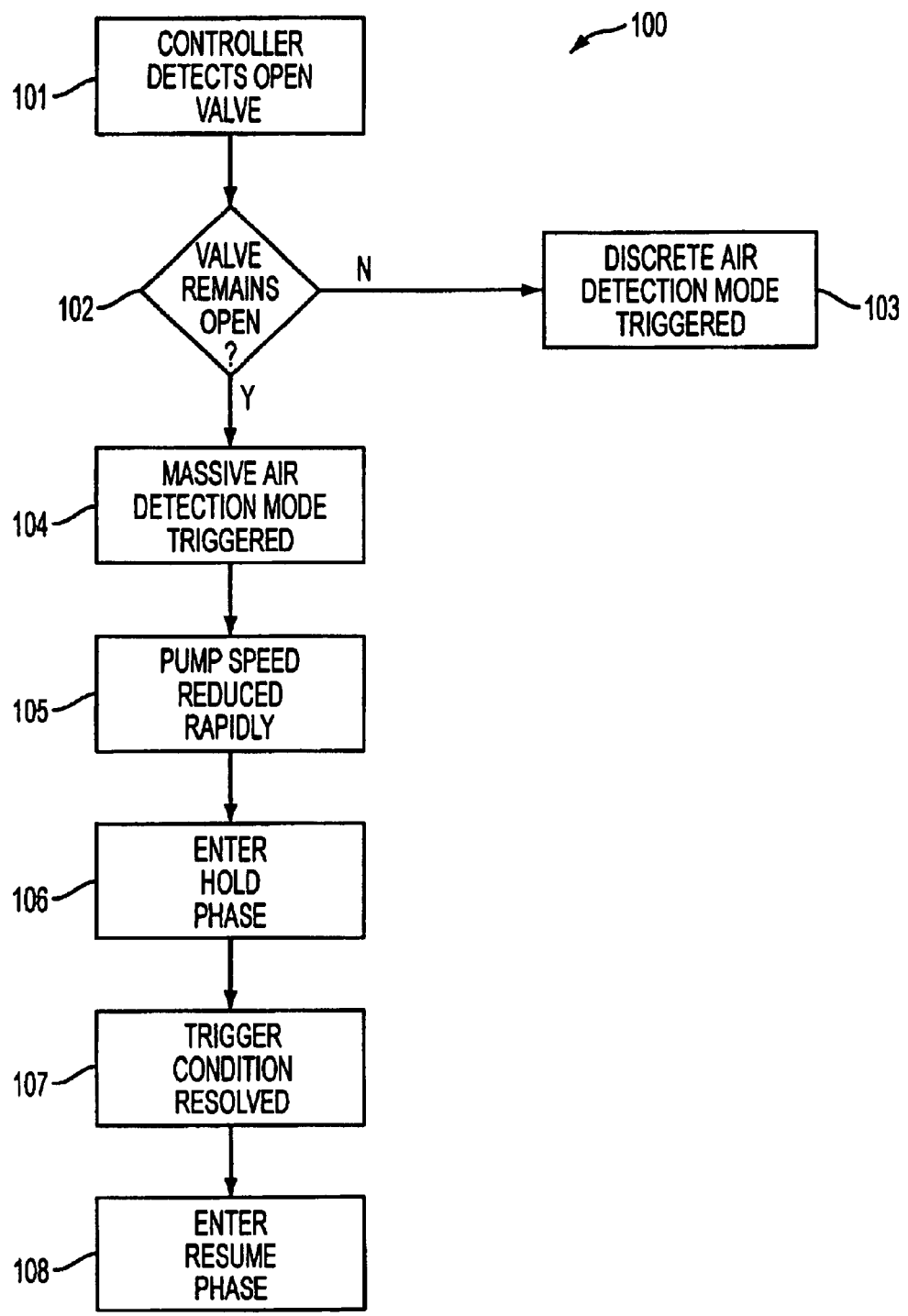
FIG. 7 is a flowchart depicting a first operational mode of the automatic flow control feature of the present invention for handling introduction of a massive bolus of air.

A first mode of operation is designed to handle the introduction of a large bolus of air into extracorporeal system 10—the "massive air detection mode." This is a high priority mode that is triggered when valve 36 (see FIG. 1) is opened to remove a large amount of air from gas collection plenum 50. Referring to FIG. 7, method 100 of automatic flow control is now described. At step 101, controller 33 detects the opening of valve 36 in response to gas within gas collection plenum 50 (see FIG. 1). At step 102, controller 33 checks whether valve 36 remains open for a predetermined duration. If so, the first operational mode is triggered (step 104) and controller 33 reacts by rapidly dropping the pump speed to the predetermined lower limit (step 105). According to a preferred embodiment, the predetermined lower limit is 1800 RPM.

At step 106, the automatic flow control enters the hold phase, wherein pump speed is maintained at the predetermined lower limit until the trigger condition is resolved (step 107) and the perfusionist enables the resume phase (step 108). During the resume phase, pump speed is gradually increased back to the initial level set by the perfusionist.

If valve 36 closes before the expiration of the predetermined duration, a second mode of operation—"the discrete air detection mode"—is triggered at step 103. The discrete air detection mode is designed to handle the presence of discrete boluses of air in the venous blood. This is a medium priority mode that is triggered when valve 36 is briefly opened to remove discrete amounts of gas from the extracorporeal blood handling system 10.

Figure 8:
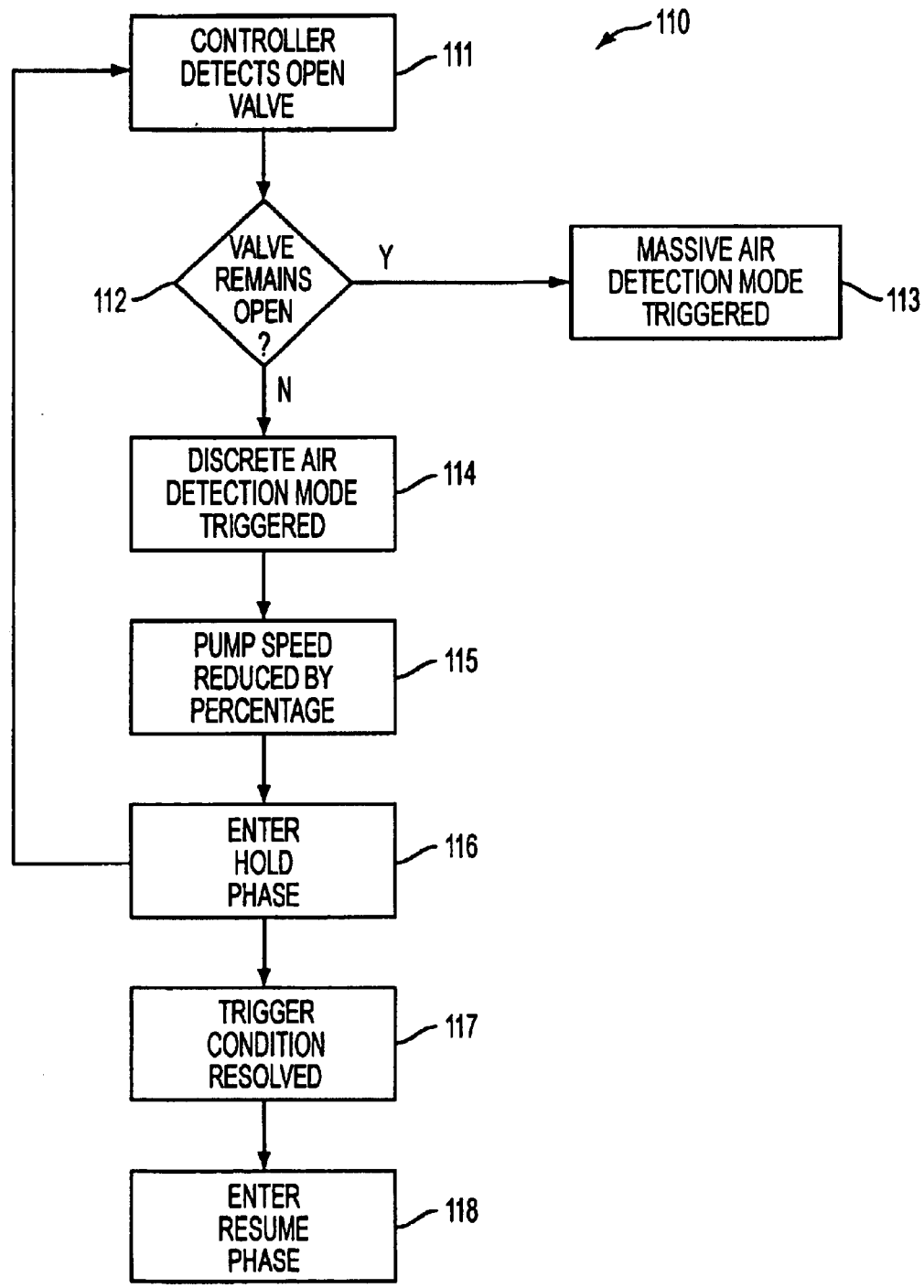
FIG. 8 is a flowchart depicting a first operational mode of the automatic flow control feature of the present invention for handling introduction of discrete, relatively small boluses of air.

Referring to FIG. 8, method 110 of automatic flow control following detection of discrete quantities of air is described. At step 111, valve 36 is opened to remove a discrete amount of gas from gas collection plenum 50 (see FIG. 1). At step 112, controller 33 checks whether valve 36 remains open for a predetermined minimum amount of time. If valve 36 remains open for more than the predetermined minimum amount of time, the massive air detection mode of FIG. 7 is triggered at step 113. The discrete air detection mode is triggered at step 114 if valve 36 closes before the predetermined amount of time has elapsed.

At step 115, controller 33 reacts by rapidly dropping the pump speed by a predetermined percentage; the algorithm then enters a hold phase. In the hold phase, pump speed is maintained at the current level until either the trigger condition is resolved (step 117) or sensor 25 detects further discrete amounts of air, in which case the method proceeds to step 111. After the trigger condition is resolved (step 117), the perfusionist enables the resume phase (step 118). In a preferred embodiment, the predetermined lower limit for the pump speed in the discrete air detection mode is 2500 RPM. If pump speed reaches this level, automatic flow control will remain in the hold phase (step 116) until the trigger condition is resolved (step 117) and the perfusionist enables the resume phase (step 118).

Figure 9:
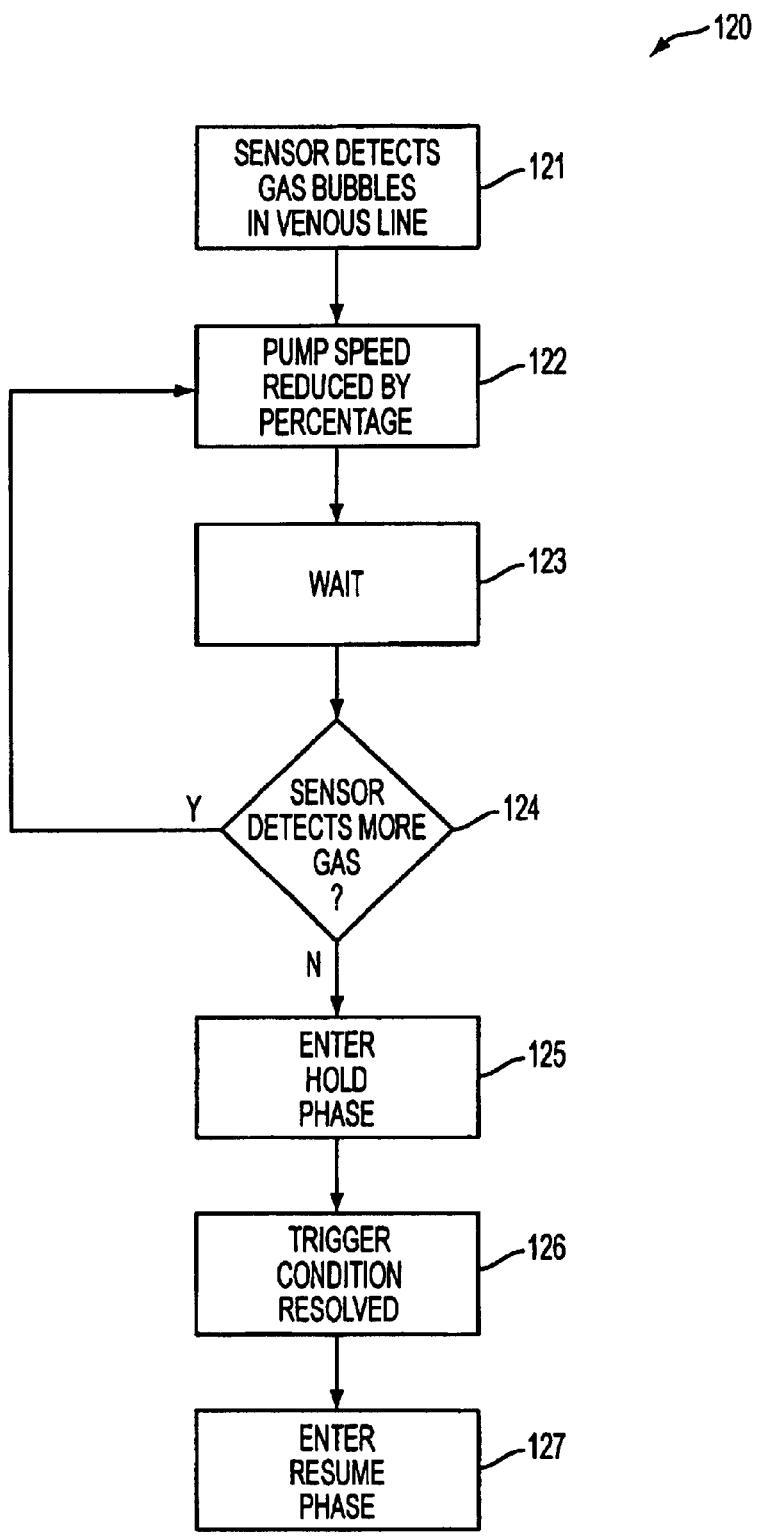
FIG. 9 is a flowchart depicting a third operational mode of the automatic flow control feature of the present invention for handling the occurrence of bubbles in the venous line.

A third operational mode—"the bubble detection mode"—is designed to handle the presence of bubbles in the venous line. This is a medium priority mode, and is triggered when sensor 26 detects gas bubbles in venous line 12. Referring to FIG. 9, method 120 of automatic flow control following bubble detection in venous line 12 is described. At step 121, sensor 26 detects the presence of gas bubbles in venous line 12 (see FIG. 1). At step 122, controller 33 reacts by rapidly lowering the pump speed by a predetermined percentage. Next, controller 33 waits for a predetermined duration (step 123) before checking the status of sensor 26. At step 124, controller 33 determines whether sensor 26 continues to detect the presence of gas bubbles in venous line 12. If gas bubbles remain in venous line 12, the method proceeds to step 122, wherein controller 33 further reduces pump speed by a predetermined percentage.

However, if the gas bubbles have dissipated, the automatic flow control system enters a hold phase at step 125. In the hold phase, pump speed is maintained at the then-current level until the trigger condition has been resolved (step 126) and the perfusionist enables the resume phase (step 127). In a preferred embodiment, the predetermined lower limit for pump speed in the bubble detection mode is 2500 RPM. If pump speed reaches this level, automatic flow control will remain in the hold phase (step 125) until the trigger condition is resolved (step 126) and the perfusionist enables the resume phase (step 127). Alternatively, controller 33 may be programmed to enter the resume phase automatically if no further bubbles are detected within a predetermined time period.

Figure 10:
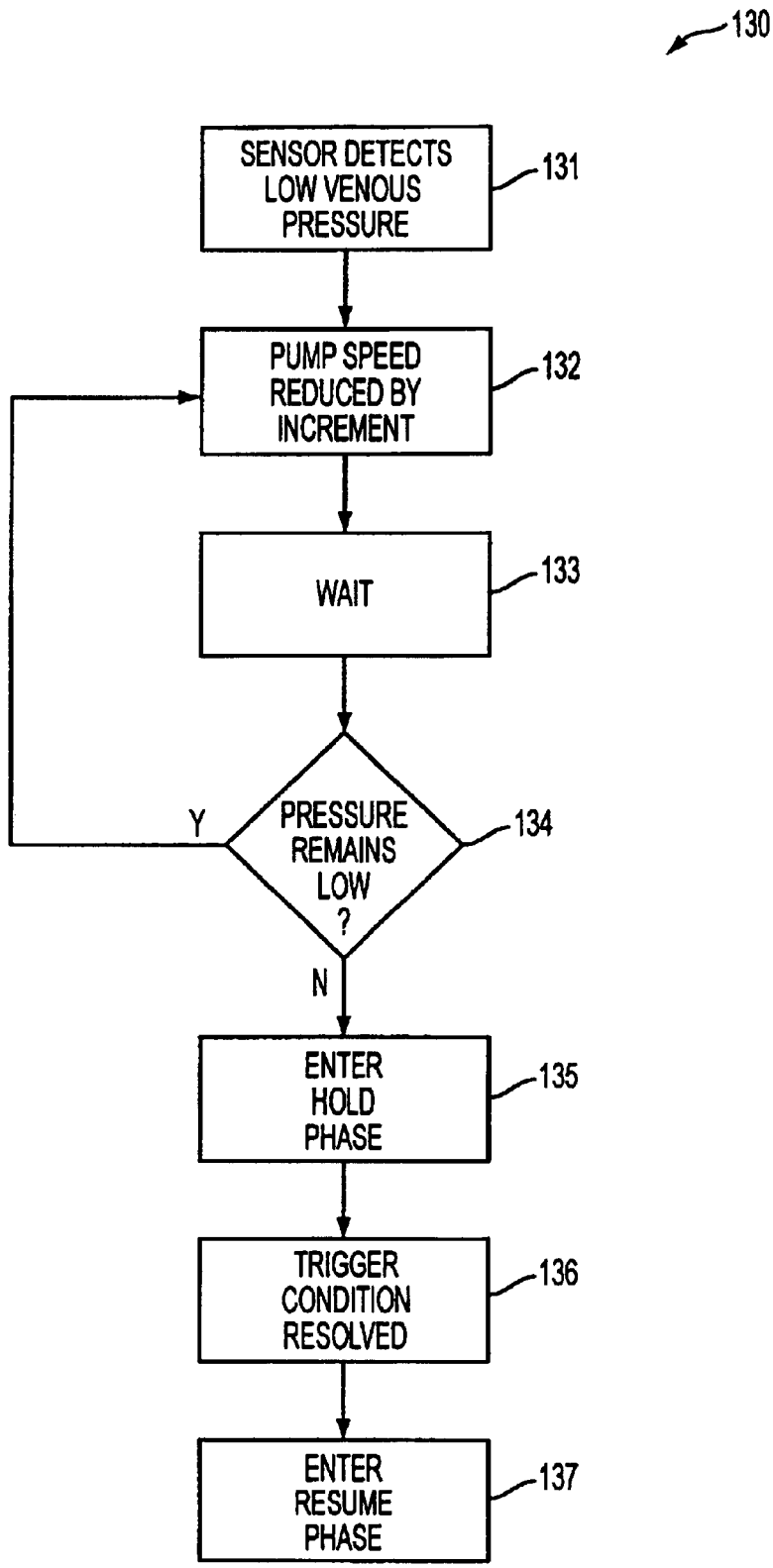
FIG. 10 is a flowchart depicting a fourth operational mode of the automatic flow control feature of the present invention for handling low venous pressure.

A further operational mode—"the low venous pressure detection mode"—is designed to handle low venous pressure in venous line 12. This is a low priority mode, and is triggered when sensor 27 detects low venous pressure in venous line 12. Referring to FIG. 10, method 130 of automatic flow control following low venous pressure detection is described. At step 131, sensor 27 detects that the venous line pressure has fallen below a predetermined threshold for a predetermined minimum duration. At step 132, controller 33 reacts by lowering the pump speed by a predetermined increment. Next, controller 33 waits for a predetermined duration (step 133) to allow conditions to stabilize. Then, at step 134, controller 33 determines whether sensor 27 continues to detect low venous pressure in venous line 12. If venous pressure remains below the predetermined threshold, then the method proceeds to step 132 and controller 33 further reduces the pump speed by the predetermined increment.

If venous pressure is no longer below the predetermined value, automatic flow control algorithm enters a hold phase (step 135). In the hold phase, pump speed is maintained at then-current level until the trigger condition is resolved (step 136) and the perfusionist enables the resume phase (step 137). In a preferred embodiment, the predetermined lower limit for pump speed in the low venous pressure detection mode is 1800 RPM. If pump speed reaches this level, automatic flow control will remain in the hold phase (step 135) until the trigger condition is resolved (step 136) and the perfusionist enables the resume phase (step 137). Controller 33 also may be programmed to enter the resume phase automatically when the pressure in venous line 12 is detected to exceed a preset level for a predetermined time period.

In the event that multiple reduction modes are triggered at the same time, the highest priority mode will take precedence. According to a preferred embodiment, the massive air detection mode is the highest priority mode followed by the discrete air detection mode, the bubble detection mode and the low venous pressure detection mode. In cases where a lower priority mode is interrupted by a higher priority mode, control returns to the lower priority mode only after the trigger condition causing the higher priority mode has been resolved. By way of example, if discrete air is sensed by sensor 25 during low venous pressure detection mode, then the automatic flow control system automatically switches to the discrete air detection mode. After the discrete air detection mode trigger condition (i.e., the presence of discrete amounts of air in the gas collection plenum) has been resolved, automatic flow control automatically returns to the low venous pressure detection mode.

Figure 11A:
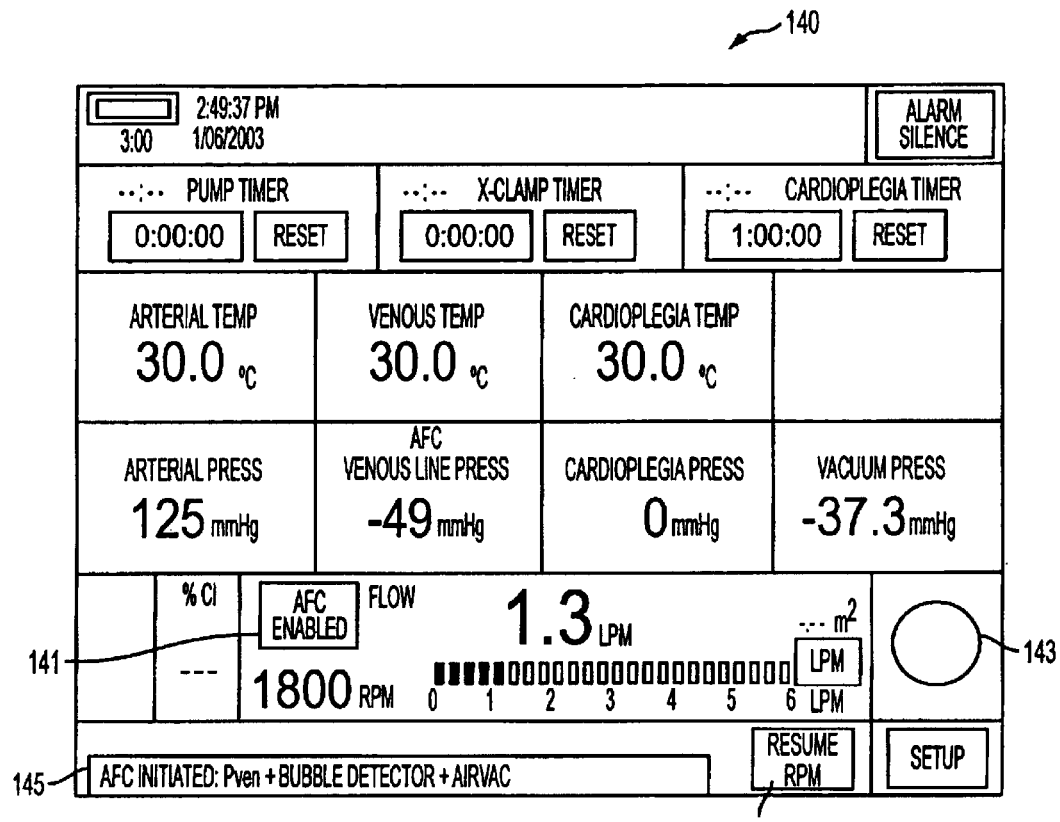
FIG. 11A is a representative screen depicting the display of parameters monitored and/or controlled by the automatic flow control feature of the present invention.

FIG. 11A is an illustrative display of main screen 140, similar to FIG. 6, that incorporates the automatic flow control system of the present invention. As will be understood by one of ordinary skill in the art of computer-controlled equipment, the software used to program operation of controller 33 may include a number of set-up screens to adjust particular system parameters. FIG. 11A depicts screen 140 that will most commonly be displayed by the perfusionist during automatic flow control.

As shown in FIG. 11A, main screen 140 includes a series of timers for pump operation, duration of cross-clamping, and a cardioplegia timer, arterial and venous temperatures and pressures, as measured, for example, at the blood inlet and blood outlet of the blood processing component 31, the speed of the centrifugal pump (RPM) and the corresponding blood flow rate.

Controller 33 preferably is programmed with a number of algorithms for determining appropriate blood flow rates and pump speeds during the procedure and for evaluating the outputs of sensors 25–27 in accordance with methods 100, 110, 120 and 130 described hereinabove. Controller 33 also preferably includes storage that is programmed with default values for the pump speed limit values, sensor threshold values, and time periods for invoking and exiting the various operational modes. Alternatively, these values may be computed based on target flow rate values computed, for example, based on the patient's BSA value, or these values may be input directly via an alpha-numeric display mode of screen 140 (not shown).

In addition, a portion of main screen 140 includes touch sensitive buttons that permit access to the other available functions. More particularly, main screen 140 includes button 141 for manually overriding automatic flow control. With this feature, a perfusionist may at any time disable or partially disable the automatic flow control system by pressing button 141. Button 141 functions both as a system control and a prominent indicator of the automatic flow control status. To increase its visibility to a perfusionist, button 141 preferably is optionally located in the region of screen 140 that includes pump speed and flow values.

Figure 11B:
FIG. 11B is a representation depicting the various states of the automatic flow control button of the present invention.

As illustrated in FIG. 11B, button 141 preferably has three states including an enabled state ("AFC ENABLED") which responds to all trigger events, a partially disabled state ("AFC NO Pven") which does not respond to low venous line pressure and a disabled state ("AFC DISABLED"). Optionally, button 141 includes different shades or colors as a further visual indication of automatic flow control system status. According to a preferred embodiment, button 141 has a green tint to indicate that automatic flow control is enabled, a yellow tint to indicate automatic flow control is partially disabled and a red tint to indicate automatic flow control is disabled.

Referring again to FIG. 11A, main screen 140 also includes button 142 to be used after resolving the trigger condition(s). Pressing button 142 gradually increases pump speed back to the initial level (i.e., the pump speed at which the first trigger condition occurred). Optionally, button 142 is darkened when pump speed returns to the initial level and/or when automatic flow control is re-triggered.

The system also optionally includes knob 143 for manually controlling the flow rate within the extracorporeal blood circuit 11. Activating (i.e., turning) knob 143 immediately returns blood handling system 10 to normal operation and darkens button 142. Using knob 143, a perfusionist may manually control how quickly the pump speed and flow rate are returned to their initial levels following automatic flow control.

Main screen 140 further may include status bar 144 to present system status and/or help messages. These messages are optionally displayed on the display unit during reduction and hold phases to indicate the present mode or modes of operation. As shown in FIG. 11A, status bar 144 indicates that automatic flow control was enabled due to a combination of the presence of discrete air in the system and low venous pressure. However, since these trigger conditions have cleared, button 142 is available. The status messages are removed if button 142 is pressed or knob 143 is activated. When button 142 is pressed, the message "AFC Resuming RPM" is displayed.

Figure 12A:
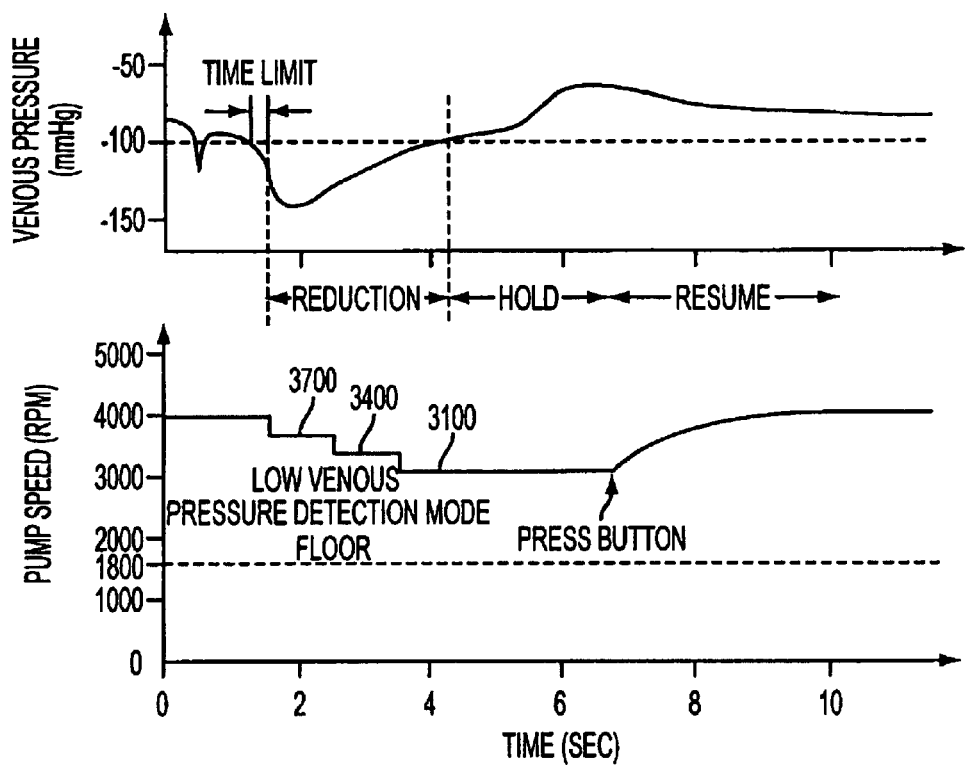
FIG. 12A is a graph showing how the automatic flow control system responds to the detection of low venous pressure trigger over time.
Figure 12B:
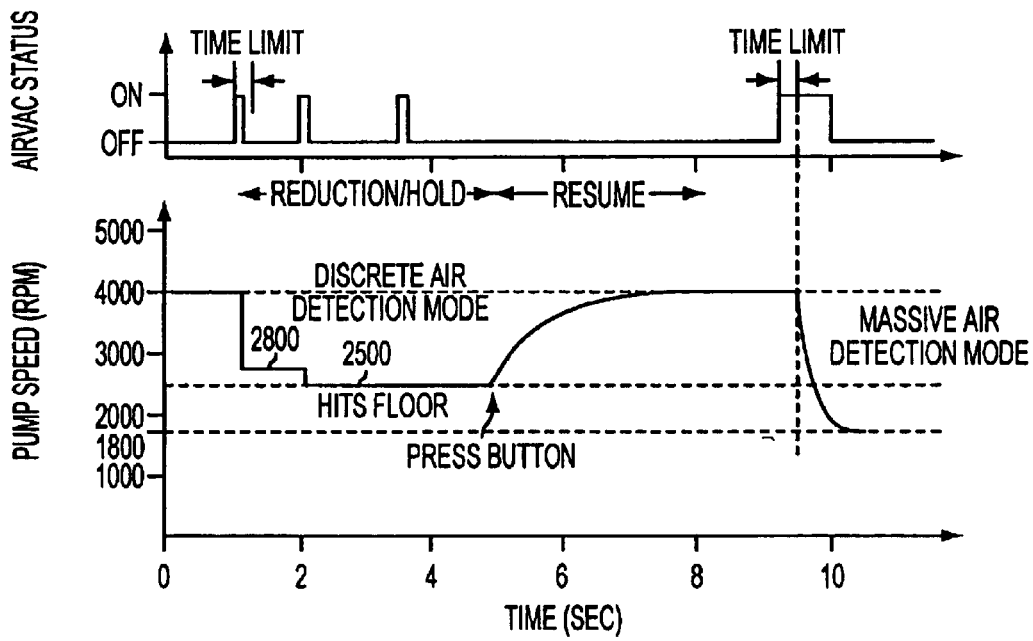
FIG. 12B is a graph showing how the automatic flow control system responds to the detection of gas over time.

FIGS. 12A and 12B are illustrative graphs showing how the automatic flow control system responds to various triggers over time. For exemplary purposes, actual values for variables such as pressure, pump speed and time, are described below in parentheses.

FIG. 12A is a graph depicting how the automatic flow control system responds over time to a low venous pressure trigger. Initially, venous pressure drops briefly below a predetermined threshold (−100 mmHg), but not for a predetermined minimum duration (2 sec). Thus, the low venous pressure detection mode is not triggered. Thereafter, venous pressure drops below the predetermined threshold (−100 mmHg) for a duration exceeding a predetermined minimum duration (2 sec) and the low venous pressure detection mode is triggered. The automatic flow control algorithms cause the pump speed to be reduced by a predetermined increment (e.g., 300 RPM) from 4000 to 3700 RPM. After waiting for a predetermined period of time (1 sec), the venous pressure is evaluated by controller 33 using the output of sensor 27, and is determined still to be below the predetermined threshold (−100 mmHg). Thus, pump speed is again reduced by the predetermined increment (300 RPM) from 3700 to 3400 RPM.

After waiting for an additional period of predetermined duration (e.g., 1 sec), the venous pressure is again evaluated, and the pump speed is reduced for a third time by the predetermined increment (300 RPM) from 3400 to 3100 RPM. This time, when venous pressure is evaluated, it is above the predetermined threshold (−100 mmHg). The automatic flow control system now enters the hold phase, in which the pump speed (3100 RPM) is maintained until the perfusionist can resolve the trigger condition. After resolving the trigger condition, the venous pressure increases (to −60 mmHg) and the perfusionist presses button 142 to signal automatic flow control to begin the resume phase. During the resume phase, pump speed is increased non-linearly over a period of time (5–6 sec) to the initial level (4000 RPM).

FIG. 12B is a graph depicting how the automatic flow control system responds over time to the detection of various amounts of air in the extracorporeal blood handling system 10. As shown in FIG. 12B, the automatic flow control system initially responds to a discrete air trigger and then responds to a massive air trigger. At the outset, valve 36 opens momentarily. Since valve 36 remains open for less than a predetermined duration (¼ sec), the discrete air detection mode is triggered instead of the massive air detection mode. The automatic flow control system rapidly decreases pump speed by a predetermined percentage (by 30% of initial RPM=4000×0.3=1200 RPM) to a new level (4000 RPM−1200 RPM=2800 RPM). Then, automatic flow control begins a hold phase at the new pump speed (2800 RPM). Next, valve 36 again opens momentarily for less than the predetermined duration (¼ sec) triggering another rapid reduction in pump speed by the predetermined percentage (by 30% of 2800 RPM=840 RPM) toward a new level (2800 RPM−840 RPM=1960 RPM).

However, before reaching the new level (1960 RPM), the pump speed hits the predetermined lower limit speed (2500 RPM) and automatic flow control begins a hold phase at the predetermined lower limit pump speed (2500 RPM). When valve 36 again opens momentarily for less than the predetermined duration (¼ sec), pump speed stays at the lower limit value (2500 RPM). Once the perfusionist corrects the problem and presses button 142, pump speed is increased non-linearly over a period of time (5–6 sec) to the initial level (4000 RPM).

Subsequently, valve 36 again opens, but this time for greater than the predetermined duration (¼ sec) and the massive air detection mode is triggered. In this case, the automatic flow control system rapidly reduces the pump speed to the predetermined lower limit for this mode of operation (1800 RPM).

Figure 13:
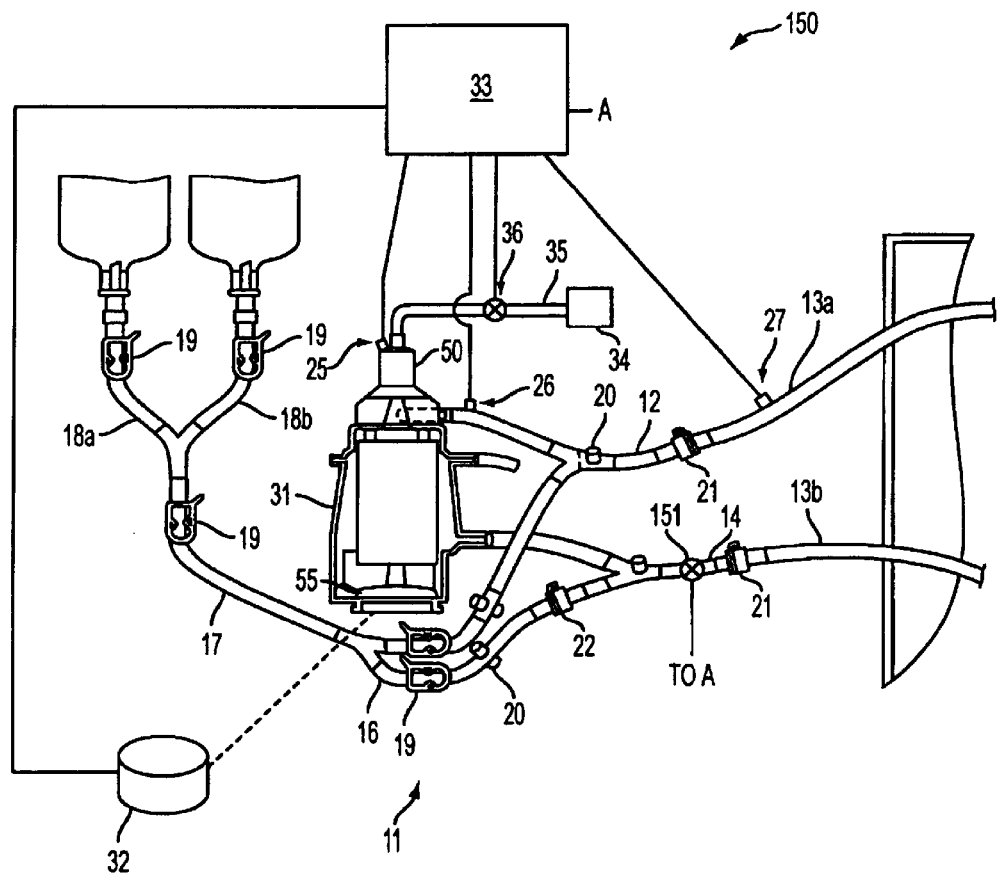
FIG. 13 is a schematic view of an alternative embodiment of an extracorporeal circuit incorporating an automatic flow control system constructed in accordance with the principles of the present invention.

Referring now to FIG. 13, an alternative embodiment of an automatic flow control system in accordance with the principles of the present invention is described. Blood processing system 150 includes all of the components blood processing system 10 described in FIG. 1, including microprocessor-based controller 33. Unlike the embodiment of the automatic flow control system described above with respect to FIGS. 7–12, the automatic flow control system of FIG. 13 uses solenoid-controlled pinch valve 151, or other suitable valve, to restrict flow to arterial line 14, rather than relying on modulation of the pump speed.

Valve 151 is coupled to controller 33, and is activated by controller 33 responsive to outputs generated by sensors 25, 26 and 27. Controller 33 may be programmed with multiple operational modes, as described hereinabove, and selectively restricts the flow through arterial line 14, either with or without pump speed modulation. For example, in a discrete air detection mode, controller 33 activates valve 151 to constrict the flow diameter by a predetermined percentage (e.g., 50%). This constriction reduces flow through the arterial line, and creates a backpressure that reduces the output flow rate of the centrifugal pump. This reduction in flow rate through the pump consequently extends the residence time of blood flowing through filter 56 and gas collection plenum 50 (see FIG. 3), and thereby enhances the ability of the gas removal system to evacuate gas from the blood processing system.

As another example, controller 33 may be programmed with algorithms that provide a massive air detection operational mode, in which valve 151 is actuated to reduce the flow rate through arterial line by 80%. In addition, the controller also may reduce the pump speed, thereby extending the time during which the perfusionist can correct the trigger condition and avoid de-priming of the blood processing component 31. Controller 33 may be programmed to modulate valve 151, either alone or in conjunction with pump speed, to implement strategies for handling the presence of bubbles or low pressure in venous line 12.

Figure 14:
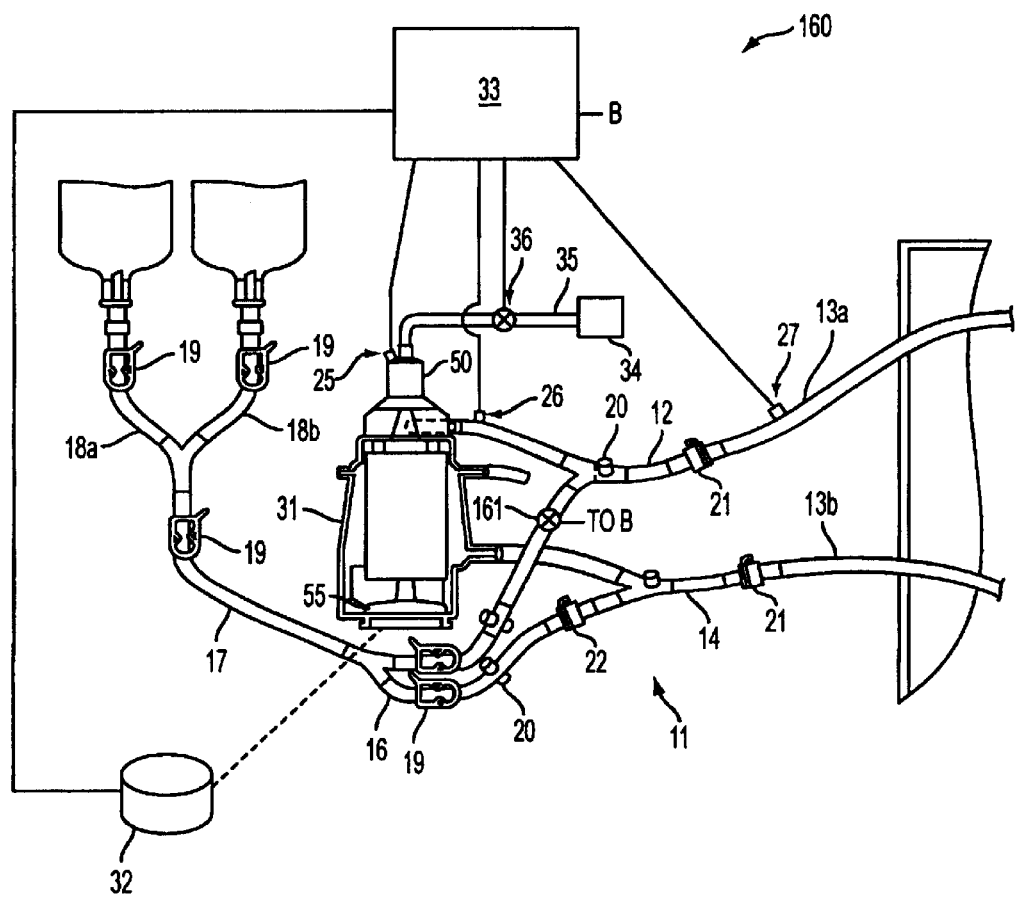
FIG. 14 is a schematic view of another alternative embodiment of an extracorporeal circuit incorporating the automatic flow control system constructed in accordance with the principles of the present invention.

Referring to FIG. 14, a further alternative embodiment of an automatic flow control system in accordance with the principles of the present invention is described. Blood processing system 160 includes all of the components blood processing system 10 described in FIG. 1, including microprocessor-based controller 33. Unlike the previously-described embodiments of the automatic flow control system, the automatic flow control system of FIG. 14 uses solenoid-controlled pinch valve 161, or other suitable valve, to selectively open a recirculation loop using the priming circuit.

Valve 161 is coupled to controller 33, and is activated by controller 33 responsive to outputs generated by sensors 25, 26 and 27. Controller 33 may be programmed with multiple operational modes, as described hereinabove, and selectively opens a bypass or recirculation loop between the outlet and inlet of blood processing component 31. Valve 161 may be used either alone, or in conjunction with modulation of pump speed, arterial line constriction, or both.

For example, in a discrete air detection mode, controller 33 activates valve 161 to fully open valve 161 from either a partially or completely closed configuration. The creation of a bypass flow path reduces flow through the arterial line, and preferentially shunts the output of the centrifugal pump to the inlet of blood processing component 31. The reduction in flow rate to the arterial line reduces the risk of perfusing air-laden blood to the patient. Moreover, recirculating the blood to the inlet of blood processing component 31 consequently extends the residence time of blood flowing through filter 56 and gas collection plenum 50 (see FIG. 3), and enhances the ability of the gas removal system to evacuate gas from the blood processing system.

Controller 33 also may be programmed with algorithms that provide a massive air detection operational mode, in which valve 161 is actuated to bypass a substantial portion of the blood flow at the outlet of blood processing component 31 to the inlet of component 31. In addition, the controller also may reduce the pump speed, and actuate valve 151 (if present) to extend the time during which the perfusionist can correct the trigger condition and avoid de-priming of the blood processing component 31. Controller 33 may be programmed to modulate valve 161, either alone or in conjunction with pump speed, to implement strategies for handling the presence of bubbles or low pressure in venous line 12.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. An apparatus for processing blood in an extracorporeal circuit, comprising:
   a venous line;
   an arterial line;
   a blood processing system having a pump, a filter having a gas collection plenum and an oxygenator, the blood processing system having an inlet to receive blood from a patient via the venous line and an outlet for reperfusing blood to the patient via the arterial line, the pump operably coupled to the filter to communicate suction to the venous line;
   a sensor coupled to the gas collection plenum to detect the presence of air in the venous line or filter and generates an output; and
   a controller programmed to modulate operation of a speed of the pump responsive to the output while retaining some forward flow through the arterial line to the patient.

2. The apparatus of claim 1, wherein the controller is programmed to reduce the speed of the pump responsive to the output.

3. The apparatus of claim 2, further comprising a valve coupled to a vacuum source, wherein the valve is configured to be selectively actuated by the controller responsive to the output of the sensor.

4. The apparatus of claim 3, wherein the controller further is responsive to duration of actuation of the valve.

5. The apparatus of claim 2, wherein the speed pump is reduced to a predetermined limit value or by a predetermined percentage.

6. The apparatus of claim 2, wherein the speed of the pump is reduced in predetermined absolute or percentage increments.

7. The apparatus of claim 1, wherein the sensor is disposed on the venous line.

8. The apparatus of claim 7, wherein the sensor monitors pressure in the venous line.

9. The apparatus of claim 7, wherein the sensor is a bubble detector.

10. The apparatus of claim 1, wherein the blood processing system further comprises a valve operably coupled to the arterial line, and the controller modulates operation of the blood processing system by changing a configuration of the valve.

11. The apparatus of claim 10, wherein the controller further modulates operation of the blood processing system by reducing a speed of the pump.

12. The apparatus of claim 1, wherein the blood processing system further comprises a recirculation line disposed between the inlet and the outlet and a valve operable coupled to the recirculation line, and the controller modulates operation of the blood processing system by changing a configuration of the valve.

13. The apparatus of claim 12, wherein the controller further modulates operation of the blood processing system by reducing a speed of the pump.

14. An apparatus for processing blood in an extracorporeal circuit, comprising:
   a venous line;
   an arterial line;
   a blood processing system including a pump, a filter having an air collection plenum and an oxygenator, the blood processing system having an inlet to receive blood from a patient via the venous line and an outlet for reperfusing blood to the patient via the arterial line;
   a sensor operably coupled to the filter to generate an output;
   a valve coupled to the filter to selectively remove air from the air collection plenum; and a controller programmed to modulate operation of the valve and the pump responsive to the output while retaining some forward flow through the arterial line to the patient.

15. The apparatus of claim 14, wherein the controlled is programmed to reduce a speed of the pump responsive to the output.

16. The apparatus of claim 15, wherein the valve is coupled to a vacuum source.

17. The apparatus of claim 15, wherein the speed of the pump is reduced to a predetermined limit value or by a predetermined percentage.

18. The apparatus of claim 15, wherein the speed of the pump is reduced in predetermined absolute or percentage increments.

19. The apparatus of claim 14, wherein the controller further is responsive to duration of actuation of the valve.

20. The apparatus of claim 14, further comprising a sensor is disposed on the venous line.

21. The apparatus of claim 20, wherein the sensor is a bubble detector.

22. The apparatus of claim 20, wherein the sensor monitors pressure in the venous line.

23. The apparatus of claim 14, wherein the blood processing system further comprises a valve operable coupled to the arterial line, and the controller modulates operation of the blood processing system by changing a configuration of the valve.

24. The apparatus of claim 23, wherein the controller further modulates operation of the blood processing system by reducing a speed of the pump.

25. The apparatus of claim 14, wherein the blood processing system further comprises a recirculation line disposed between the inlet and the outlet and a valve operable coupled to the recirculation line, and the controller modulates operation of the blood processing system by changing a configuration of the valve.

26. The apparatus of claim 25, wherein the controller further modulates operation of the blood processing system by reducing a speed of the pump.

* * * * *